United States Patent [19]

Rogozinski

[11] Patent Number: 5,102,412
[45] Date of Patent: Apr. 7, 1992

[54] SYSTEM FOR INSTRUMENTATION OF THE SPINE IN THE TREATMENT OF SPINAL DEFORMITIES

[76] Inventor: Chaim Rogozinski, 4453 Forest Dr. S., Jacksonville, Fla. 32216

[21] Appl. No.: 540,635

[22] Filed: Jun. 19, 1990

[51] Int. Cl.$^5$ .............................................. A61F 5/00
[52] U.S. Cl. ......................................... 606/61; 606/72
[58] Field of Search .................... 606/61, 53, 60, 61, 606/62, 64, 69, 71, 74; 128/69

[56] References Cited

U.S. PATENT DOCUMENTS

| | | | |
|---|---|---|---|
| 4,269,178 | 5/1981 | Kline | 606/61 |
| 4,347,845 | 9/1982 | Mayfield | 606/61 |
| 4,369,770 | 1/1983 | Bacal et al. | 606/61 |
| 4,382,438 | 5/1983 | Jacobs | 606/61 |
| 4,409,968 | 10/1983 | Drummond | 128/69 |
| 4,422,451 | 12/1983 | Kalamchi | 606/61 |
| 4,567,884 | 2/1986 | Edwards | 606/61 |
| 4,611,582 | 9/1986 | Duff | 128/69 |
| 4,719,905 | 1/1988 | Steffee | 606/61 X |
| 4,773,402 | 9/1988 | Asher et al. | 128/69 |
| 4,955,885 | 9/1990 | Meyers | 606/53 |

FOREIGN PATENT DOCUMENTS

| | | | |
|---|---|---|---|
| 2649042 | 1/1978 | Fed. Rep. of Germany | 128/69 |
| 2612070 | 9/1988 | France | 606/61 |
| 0348272 | 6/1989 | France | 606/61 |
| 0780652 | 8/1957 | United Kingdom | 128/69 |

OTHER PUBLICATIONS

Zimmer Spiral Instrumentation Catalog, Section D, pp. D5-D7, D24; Warsaw, IN, 46580-0708, Copyright 1987.

Primary Examiner—Richard J. Apley
Assistant Examiner—Linda C. M. Dvorak
Attorney, Agent, or Firm—Edward S. Irons; Thomas S. Hahn

[57] ABSTRACT

A spinal rod system and method for instrumenting the spine in the treatment of spinal abnormalities, in which a plurality of vertebra engaging means are provided for engagement on spaced vertebra, and the vertebra engaging means are secured on at least one elongate rod in axially spaced relationship, to impose opposed axial forces on the spine. In a preferred arrangement, two rods are used, and cross bars extend laterally between the rods to form a quadrilateral construct. The vertebra engaging means may comprise hooks, screws, or a combination of hooks and bone screws. Couplers are used to secure the screws and the transverse cross bars to the rods. The couplers and hooks all have similarly shaped and sized bodies with slotted backs opening in a posterior direction, whereby they may be interchanged in various positions relative to one another on the rods for optimum vertebral engagement, and the hooks may be first applied to the vertebra and the rods then pivoted into place for laying the rods into the slotted backs of the bodies to secure the components in place. The screw has a T-shaped head pivotally received in a coupler whereby two screws may be inserted into the pedicle of a vetebra in converging directions to obtain a mechanical lock on the vertebra.

30 Claims, 7 Drawing Sheets

SYSTEM FOR INSTRUMENTATION OF THE SPINE IN THE TREATMENT OF SPINAL DEFORMITIES

FIELD OF THE INVENTION

This invention relates generally to surgical apparatus and methods for use in the treatment of spinal deformities such as scoliosis and kyphosis, and for internal fixation of the spine. More specifically, the invention relates to a modular instrumentation system and method in which individual components of a spinal rod construct may be assembled and surgically implanted. The system and method of the invention provides much greater flexibility and ease of use for the treatment of spinal abnormalities such as curvature of the spine, fractures, and the like, when an arthrodesis is required.

DESCRIPTION OF THE PRIOR ART

Spinal deformities such as scoliosis and kyphosis, fractures and conditions which need an arthrodesis, have been treated with a variety of apparatus and methods, including external braces and traction apparatus, and surgical implants. Surgical treatment of scoliosis, for instance, is generally indicated when the lateral deviation of the spine exceeds certain limits. Such surgical treatment, known as arthrodesis, involves both correction of the curvature of the spine in the region of deviation, and fusion by autogenous bone grafts of the vertebrae in the region of abnormal curvature. In bone fusion techniques, it is imperative that a corrected and fixed configuration of the vertebrae be immobilized during the period in which vertebrae are being fused. Both posterior and anterior instrumentation has been developed for this purpose, although the posterior instrumentation is generally preferred because of the more simple surgical technique required to implement it.

One known surgical technique for maintaining corrected positioning of vertebrae during the fusion process involves the attachment of rods to the spine to obtain anatomic alignment of the spine and immobilize the spine until arthrodesis is completed. A variety of different types of instrumentation for implementing this procedure have been developed in the prior art. These prior art instrumentations utilize some form of compression and contraction-distraction apparatus that is applied to the spine to straighten the curvature. In some of these systems, the rods are secured to the spine by use of wires passed through the vertebrae and around the rods. Such systems are described, for example, in Russian patent publication Nos. 1053404 A of 1983, and 441932 of 1974.

In other systems, staples are attached by screws to the ventral or anterior side of the vertebrae on the convex side of the deformity, and the stapled vertebrae are interconnected by passing a cable through holes in the heads of the screws. Then, starting at one end, pairs of stapled vertebrae are compressed by applying tension to the cable to straighten the curve. Compression between vertebrae is maintained by crimping the screw heads onto the cable. This system of staples, screws and cable is known as Dwyer instrumentation.

Instrumentation for posterior implantation is disclosed in U.S. Pat. No. 3,565,066, in which a rigid member bridges a scoliotic, kyphotic, or lordotic curve and hooks are disposed orthogonally to the rigid member to engage and move individual vertebrae toward the rigid member.

Other instrumentation for posterior implantation includes that known as Harrington instrumentation. This system has gained the greatest acceptance, and comprises an elongate threaded rod in combination with two or more hooks that are hooked onto the lamina of respective vertebrae and secured to the rod. One rod and its associated hooks may be placed on the convex side of the deformity to apply a compressive force to the vertebrae, while a second rod and its associated hooks may be applied on the contralateral side of the deformity to apply distraction to the vertebrae. Examples of Harrington instrumentation are disclosed in U.S. Pat. Nos. 4,269,178, 4,274,401, 4,361,141, 4,369,769, 4,369,770, 4,382,438, 4,386,603, 4,404,967, 4,409,968, 4,411,259 and 4,422,451.

Other examples of prior art apparatus for treatment of spinal deformities are disclosed in Russian patent disclosure 654,251, of 1979, and U.S. Pat. Nos. 3,242,922, 4,448,191, 4,567,884 and 4,611,582.

As is apparent from the prior art listed above, most prior art systems use some form of elongate rod and hook structure. In many of these, the hooks are threaded onto an elongate threaded rod so that the hooks may be moved toward and away from one another on the rod to apply either distraction or compression on the vertebrae. Some devices, as disclosed by BLISKUNOV (Russia, 654,251, March 1979) and DUFF U.S. Pat. No. 4,611,582, are complex mechanisms having multiple threaded rods concentrically engaged on one another, and/or with ratchet mechanisms for adjusting the spacing between hooks.

The prior art systems have several disadvantages incident to their use. For instance, the most widely accepted system uses threaded rods on which hooks are engaged for applying compression or distraction to the vertebrae. These systems are essentially preassembled, with a predetermined number of hooks being threaded in a particular order and spacing on the rods for appropriate hooked engagement with the vertebrae. Each construct is thus specific to a particular order and spacing on the rods for appropriate hooked engagement with the vertebrae. Each construct is thus specific to a particular surgical procedure, and any change that involves repositioning, deletion or addition of hooks requires disassembly of that construct and new instrumentation for the modified construct.

Adaptation of these prior art systems to specifically encountered needs during a surgical process or treatment modality is relatively inflexible, and the surgeon is limited to use of a preassembled construct or to building of a new one. Moreover, prior art instrumentation is generally designed for correction of a specific abnormality, and is not readily adaptable for additional correction capabilities. Additionally, many prior art systems are relatively unstable torsionally or in the frontal plane, and may require the use of distraction for fixation.

The "fixed" nature of prior art constructs also sometimes requires compromise in the positioning of hooks and/or screws, leading to inherent weakness in the attachments, or undue intrusion of parts of the instrumentation into the spinal canal, or preloading of components.

Efforts at solving some of the above-described problems have led to improved instrumentation, but problems still exist. For example, one prior art system uses slotted hooks which are assembled to a rod by use of a threaded sleeve pre-positioned on the rod. In this apparatus, the hook is held with a special hook holder, while the rod and sleeve are moved transversely into the slot of the hook and then moved longitudinally to secure the sleeve within the slot, thereby securing the hook to the rod. This system requires the manipulation of sleeves and locking nuts movable along the rod to lock the hook to the rod. A specially designed hook holder is needed to use this instrumentation. Moreover, adaptation of this system to include additional hooks or delete previously installed hooks, etc. would require disassembly of the existing construct.

Further, because of the nature of the construction of prior art systems, they are not readily matched to the different anatomies of different patients. Thus, with prior art systems it may be necessary to bend or highly stress one or more components of the system in order to span the lateral dimension of the spine for bilateral attachment. Additionally, it may be necessary with prior art systems to contour the rod in order to obtain a lordotic curve. Moreover, hooks in prior art systems are not readily interchangeable with one another and compromises must be made in fitting the hooks to particular lamina. For example, the surface of some lamina may be tapered or inclined, because of shingling of the lamina, for example, and conventional hooks are not shaped to properly fit such configurations. The rigid attachment of bone screws to conventional instrumentation also results in compromises in selection of the quality of the purchase obtained by the screw, or in attachment of the screw to the rest of the instrumentation.

SUMMARY OF THE INVENTION

Accordingly, it is an object of the present invention to provide a modular system and method for surgical instrumentation of the spine in the treatment of spinal deformities such as scoliosis, kyphosis, and for obtaining interval fixation, affording the surgeon flexibility in configuring the internal fixation to the anatomic constraint of the patient without compromising fixation capabilities.

Another object of the invention is to provide a spinal instrumentation system and method in which the instrumentation may be adapted during implantation to use of either bone screws or hooks, or to use of both in combination.

A further object of the invention is to provide a spinal instrumentation system and method in which hooks or screws secured on elongate rods are used to apply compression and/or distraction to the vertebrae, and the hooks and screws are constructed so that they ma be positioned with respect to selected vertebrae, the rods laid in place with respect to the hooks and screws and then secured.

A still further object of the invention is to provide a construct for internal fixation to the spine, wherein components may be added or deleted after the construct is in place without having to dismantle the existing construct.

Yet another object of the invention is to provide a system of instrumentation for the spine, wherein elongate rods are pivotally connected with hooks and screws engaged on the vertebrae, whereby the hooks and screws may be pivoted to enable the instrumentation to be used to derotate a scoliotic curve, and to provide additional correction capabilities.

Another object of the invention is to provide an instrumentation system and method for correcting abnormalities of the spine, wherein hooks and/or screws are engaged with the vertebrae and interconnected through couplers and rods to apply compressive or distractive forces to the vertebrae, and in which the hooks and/or screws may be attached to the vertebrae and then secured to the rod by means of a locking mechanism accessible from a dorsal approach.

An even further object of the invention is to provide an improved hook design for use in spinal instrumentation, in which templating of the lamina of the vertebrae may be performed by selection of a preferred hook shape to optimize contact with the vertebrae, enabling tricortical capturing of the lamina and avoiding single point laminar contact, minimizing hook plunge into the spinal canal and compensating for shingling of the spine, and permitting the surgeon to instrument the system without having to contour a lordotic curve into the rod.

A further object of the invention is to provide a construct for spinal instrumentation in which elongate rods are secured to hooks and screws engaged with the vertebrae, and transverse cross bars extend between the rods to form a quadrilateral construct, stabilizing the rods both torsionally and in the frontal plane, and also eliminating the need for distraction for fixation.

A still further object of the invention is to provide a spinal instrumentation system in which a quadrilateral construct incorporates spaced apart convergent bone screws to form a delta configuration, enhancing the holding strength of the bone screws by forming a mechanical lock.

An even further object of the invention is to provide an instrumentation system and method for correcting abnormalities of the spine, in which bone screws and hooks may be used in combination or separately, and are interconnected by use of elongate rods, couplers and cross bars, with the hooks and/or screws being rotationally engaged with the rods, permitting the bone screw to be inserted in an optimal position and avoiding preloading of the bone screw.

Another object of the invention is to provide surgically implantable instrumentation for correcting abnormalities of the spine, in which the instrumentation comprises modular components assembled in situ, and in which each component is fixed to adjoining components with consistent force, resulting in a stable construct.

Yet a further object of the invention is to provide a construct for surgical implantation of instrumentation of the spine during arthrodesis, wherein the construct is of low profile, enabling the surgeon to perform decortication and application of the bone graft as a last step in the fusion process, thereby reducing intraoperative bleeding and morbidity associated with the surgery.

Another object is to provide a spinal instrumentation system having medially spaced elongate rods interconnected by cross bars, wherein cross bars of varying length may be selected to match the construct closely to the anatomy of the patient, avoiding the imposition of stresses in the system caused by poorly fitting components.

A still further object is to provide a spinal instrumentation system which uses hooks for engaging the lamina of the vertebrae, and in which a plurality of differently configured and sized hooks may be interchanged in the construct for optimizing contact of the hook with the lamina of the vertebrae.

An even further object is to provide a spinal instrumentation system in which a combination of hooks and screws may be used to minimize damage to joints adjoining the area being fused.

Yet a further object is to provide a spinal instrumentation system in which screws are pivotally attached to elongate rods so that the screws may be inserted into the pedicle of the vertebrae in a convergent orientation to form a mechanical lock.

These objects are achieved by a simple and effective structure and method in which hooks and/or screws are adapted to be secured on elongate rods and engaged with the vertebrae of the spine in order to apply compression to the convex side of the curvature, and distraction to the contralateral side, respectively, in the treatment of spinal deformities such as scoliosis and kyphosis, for example.

The instrumentation of the invention is modular, and comprises elongate rods adapted to extend alongside the spine, with individual hooks engaged with selected vertebrae and adjustably secured on the rods with readily accessible fasteners, such as hook bars and set screws. Cross bars and couplers may be interconnected with the rods to form a quadrilateral construct, which stabilizes the rods both torsionally and in the frontal plane. The hooks, cross bars and couplers may be selectively added to or removed from the construct by loosening the set screws and removing the hook bar, thereby releasing the hook from the rod.

The hooks are specially configured and are provided in a plurality of sizes so that an appropriate hook may be selected for optimum engagement with the lamina of each vertebrae. They also have a dorsal slot so that they may first be positioned in operative relationship with the lamina of the vertebrae, and the elongate distraction or compression rod then laid into the dorsal slot. The hooks are also interchangeable with one another in the instrumentation, enabling an appropriate hook to be selected for best fit on a given lamina. This system enables customization of the construct, and the addition of further hooks, etc., without dismantling the construct. It also greatly facilitates the task of the surgeon and minimizes the effort required to instrument the spine.

The cross bars for interconnecting two elongate rods in a construct according to the invention are provided in a plurality of varying lengths so that the construct may be closely matched to the anatomy of the patient, thus avoiding the imposition of stress on the components of the system, as might be caused by an improperly fitted device.

The interchangeability of components in the system also permits the surgeon to select either hooks or screws, or a combination of both, in making a construct. Thus, for example, a hook and screw combination could be used in order to obtain maximum purchase of the system and at the same time avoid use of a screw in the joint next to that being fused, thereby saving that joint from the damage that would be caused by use of a screw.

In the system of the invention, the screws are T-shaped and are pivotally mounted in the coupler used to attach them to the elongate rod. This permits the screws to rotate or pivot relative to the rod and enables the screws to converge as they penetrate the pedicle, forming a delta configuration and forming a mechanical lock. The screws used in the instrumentation of the invention are applied using a special driver which is engaged with the screws to turn them into the selected vertebrae.

In preparing the instrumentation of the invention, trial hooks are selected and placed in operative association with the selected lamina, then driven into final position by use of a drive mallet. These trial hooks are then used as guides to select the hook to be used in the final construct, thus enabling a close fit of the hooks on the lamina. The trial hooks actually comprise a tool in accordance with the invention, in that a mock hook is permanently affixed to the end of a handle which is used to manipulate the hook. Six different trial hooks are provided, in two different sizes for each of three different configurations.

Similarly, the hooks are initially held in position with respect to the selected lamina by use of a special hook holder that is configured with projections shaped complementally to the oval shaped openings in the hook bodies.

BRIEF DESCRIPTION OF THE DRAWINGS

The foregoing objects of the invention, as well as other objects and advantages, will become apparent from the following detailed description when it is considered in conjunction with the accompanying drawings, in which like reference characters designate like parts throughout the several views, and wherein.

DETAILED DESCRIPTION OF THE PREFERRED EMBODIMENTS

Figure 1:
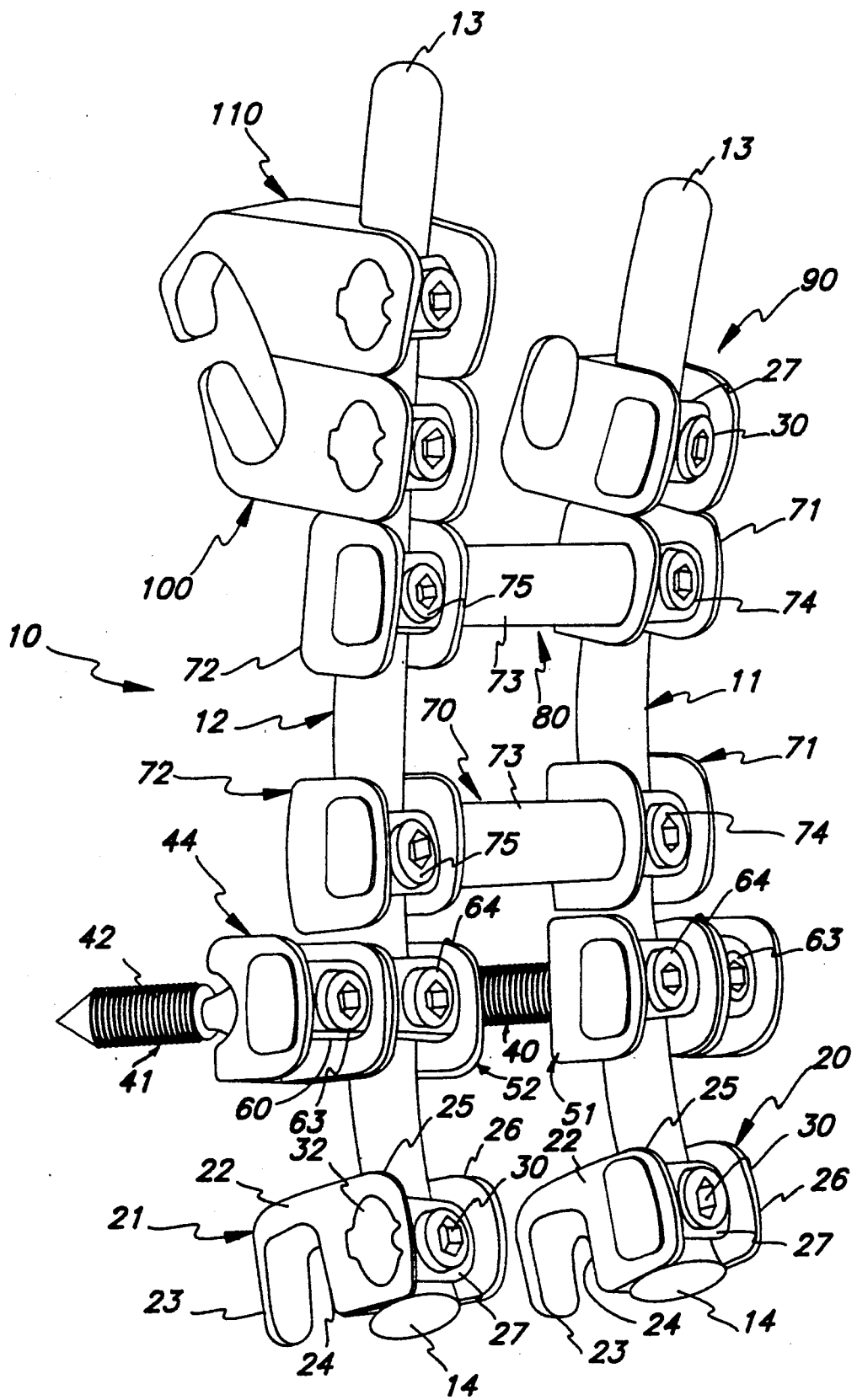
FIG. 1 is a perspective view of an assembled construct of the invention adapted for implantation between the S-1 and L-4 vertebrae, as viewed from the dorsal side.

For purposes of illustration, a spinal instrumentation system for a particular construct, i.e., extending from the level of lumbar vertebra L-4 to the S-1 lamina of the sacrum, will be illustrated and described herein. However, it is to be understood that the same principles would apply to differently configured constructs, extending over different portions of the spine.

Referring more particularly to the drawings, one version of a construct for instrumenting the spine in accordance with the invention is referenced generally as 10. As seen best in FIGS. 1 and 2, this construct comprises first and second elongate rods 11 and 12 extending generally parallel to one another, and adapted to extend on laterally opposite sides of the spine in spanning relationship to the deformity. The rods each have a smooth, rounded cephalad end 13 and a flanged or headed caudal end 14. Moreover, in the particular construct shown, the rod 12 has a greater length than the rod 11 in order to accommodate additional instrumentation, described hereinafter.

A first pair of downwardly facing hooks 20 and 21 are mounted on the caudal ends of the rods, in abutting relationship to the flanged ends 14. These hooks are of a first configuration, referred to hereinafter as neutral hooks, and have a spine 22 extending generally perpendicular to the axis of the respective rod; a downturned lip or hook 23 on the anterior end of the spine; a rear wall 24 extending from the posterior end of the spine in spaced, parallel relationship to the hook 23; and a pair of spaced apart parallel walls or flanges 25 and 26 projecting rearwardly from the wall 24. The walls or flanges 25 and 26 are spaced so as to closely engage on opposite sides of the respective rods, and the hooks are secured on the rods by a hook bar 27 extended through aligned openings 28 and 29 in the walls 25 and 26, on the posterior side of the respective rod, and fastened in place by a set screw 30 extended transversely through a threaded opening 31 in the hook bar into contact with the respective rod. In the particular instrumentation shown, these hooks are engaged on the lamina of the sacrum.

It should be noted that the openings 28 and 29 are oval in shape, and the hook bars have a corresponding oval cross section so that they will fit the openings in only one orientation. Further, the hook bars have a shaped flanged end 32 to limit insertion of the hook bars into their respective openings, and to provide a tactile and visual indication of the proper orientation of the hook bar in the openings. That is, the threaded opening 31 in the hook bars is threaded to receive the set screw 30 from only one end of the threaded opening, and it is therefore necessary that the appropriate end of the threaded opening faces in a posterior direction for receiving the set screw.

A pair of bone screws 40 and 41 are attached to the respective rods in spaced relationship to the hooks 20 and 21, for insertion into the pedicle of the S-1 vertebra in the particular construct shown. The bone screws each comprise an elongate threaded shank 42, having a T-shaped head 43 on the posterior end (FIGS. 6-9) and are carried by screw couplers 44.

The screw couplers 44 are generally U-shaped in top plan view, and each comprises an anterior wall 45 having a central opening 46 therethrough for receiving the shank 42 of the respective bone screws, and a pair of spaced apart, parallel side walls 47 and 48 extending in a posterior direction from the wall 45. Aligned, oval shaped openings 49 and 50 are formed through the side walls in spaced relationship to the wall 45.

The head 43 of the bone screw is sized and shaped to fit snugly between the side walls 47 and 48, against the anterior wall 45, and just anteriorly of the openings 49 and 50.

Second U-shaped couplers 51 and 52, constructed substantially identically to the screw couplers 44, are disposed in side-by-side, contiguous relationship to the screw couplers 44 and each has an anterior wall 53 with a pair of spaced apart parallel side walls 54 and 55 projecting rearwardly therefrom. Aligned, oval-shaped openings 56 and 57 are formed through the side walls 54 and 55. These openings are also in alignment with the corresponding openings in the screw couplers 44 when the two couplers are disposed side-by-side as shown in the drawings.

Figure 2:
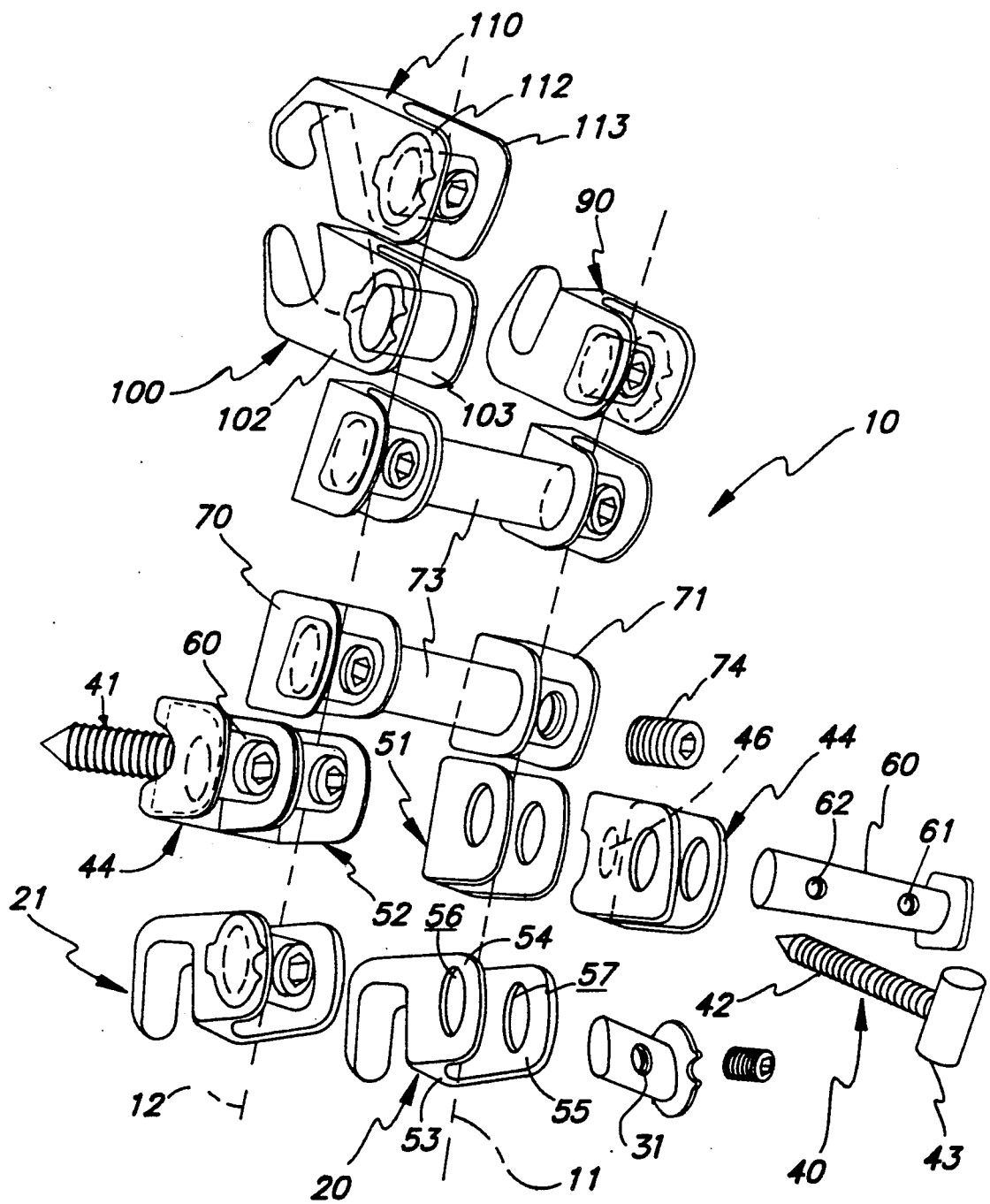
FIG. 2 is an exploded perspective view of the construct of FIG. 1, showing the various elements or components that make up the construct.
Figure 3:
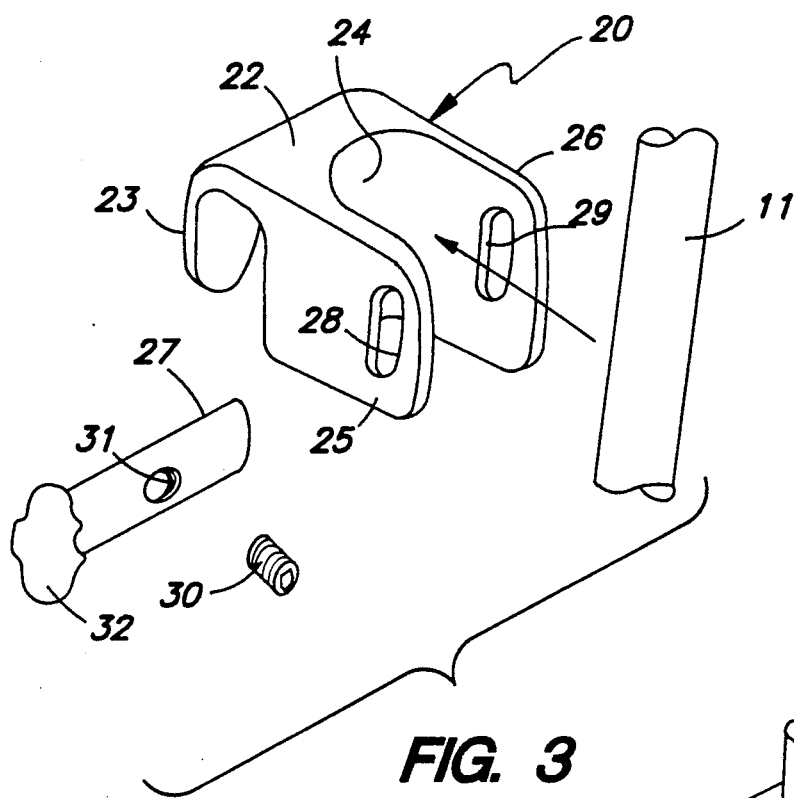
FIG. 3 is an enlarged, fragmentary, perspective, exploded view of one of the hooks of figure I, showing the hook bar and set screw used therewith in position to receive the elongate distraction or compression rod.
Figure 5:
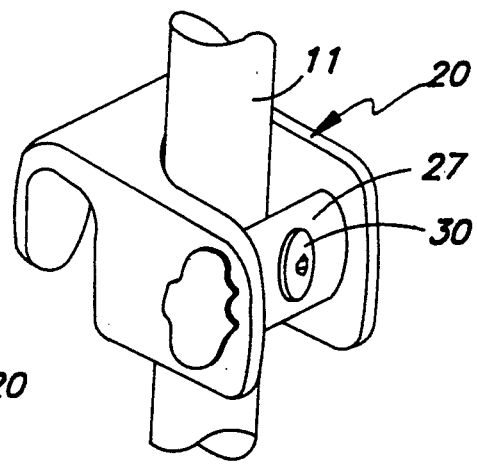
FIG. 5 is a view similar to FIG. 4, showing the rod, hook bar and set screw all in operative position to secure the hook to the rod.
Figure 4:
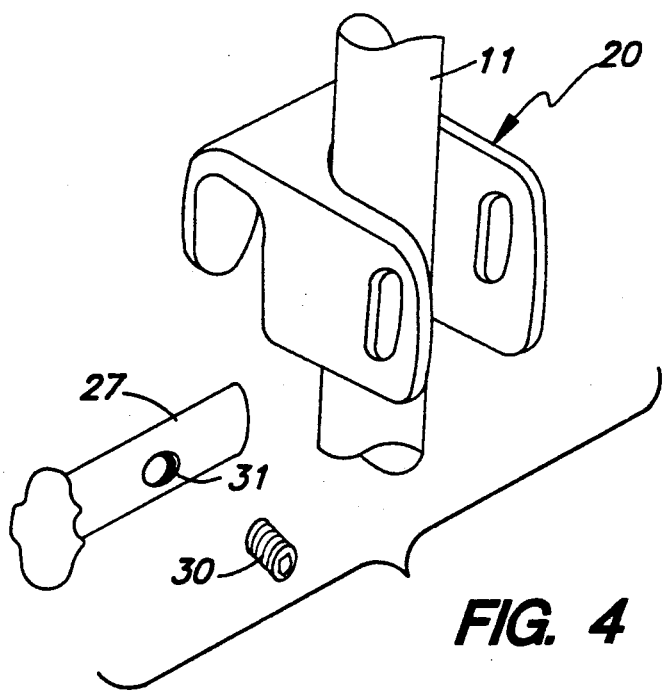
FIG. 4 is a view similar to FIG. 3, showing the rod in place in the hook body, and the hook bar about to be inserted.
Figure 6:
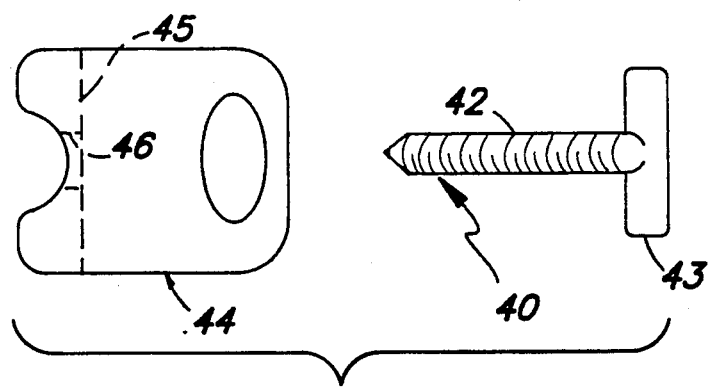
FIG. 6 is an exploded view in side elevation of a bone screw coupler and bone screw as used in the invention.
Figures 7, 8:
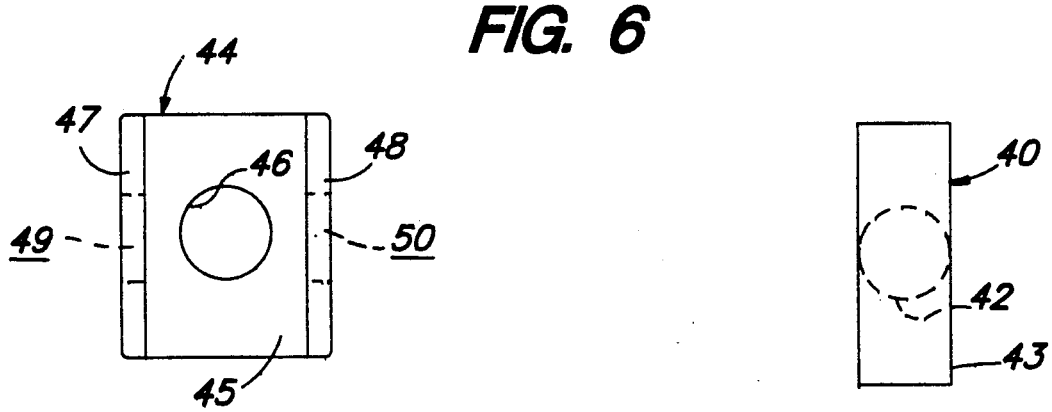
FIG. 7 is a distal end view in elevation of the bone screw coupler of FIG. 6.
FIG. 8 is a distal end view in elevation of the bone screw used in the apparatus of FIG. 6.

The coupler pairs 44, 51 and 44, 52 are held in mating relationship to one another and in secured relationship on the rods 11 and 12, as shown in FIG. 1, by cross bars 60 extended through the aligned openings in the respective couplers. The cross bars have a length sufficient to extend through the openings in both couplers of the respective pairs, and each has a first opening 61 located to be positioned midway between the side walls of the bone screw coupler 44, and a second opening 62 located to be positioned midway between the side walls of the mating coupler 51 or 52. A set screw 63 is threaded through the respective first openings and into engagement with the head 43 of the bone screws, and a set screw 64 is threaded through the respective second openings and into engagement with the rods 11 and 12, securing the screws to the screw couplers, securing the coupler pairs together, and securing the entire assembly to the rods.

Figure 9:
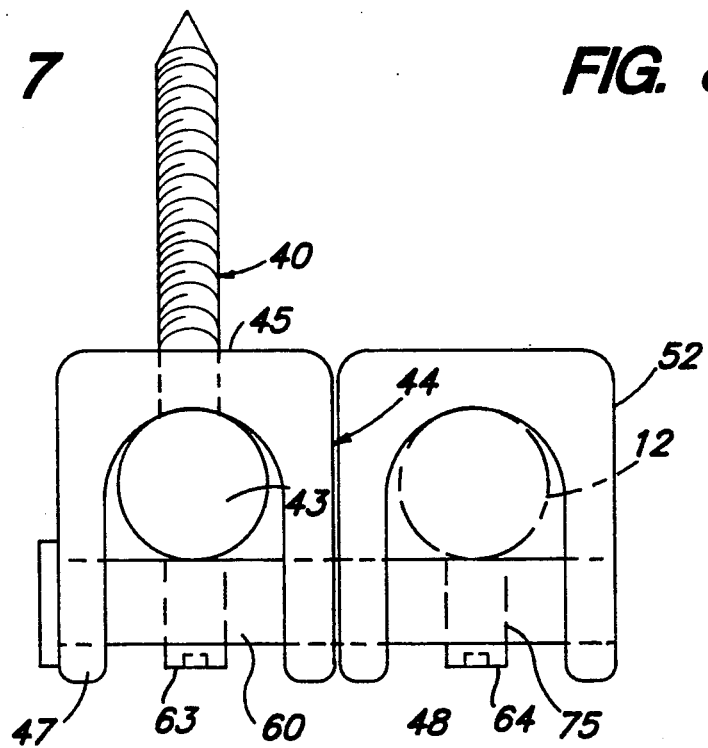
FIG. 9 is a top plan view of a bone screw coupler, bone screw, cross bar and set screw as used in the apparatus of FIG. 6.
Figure 10:
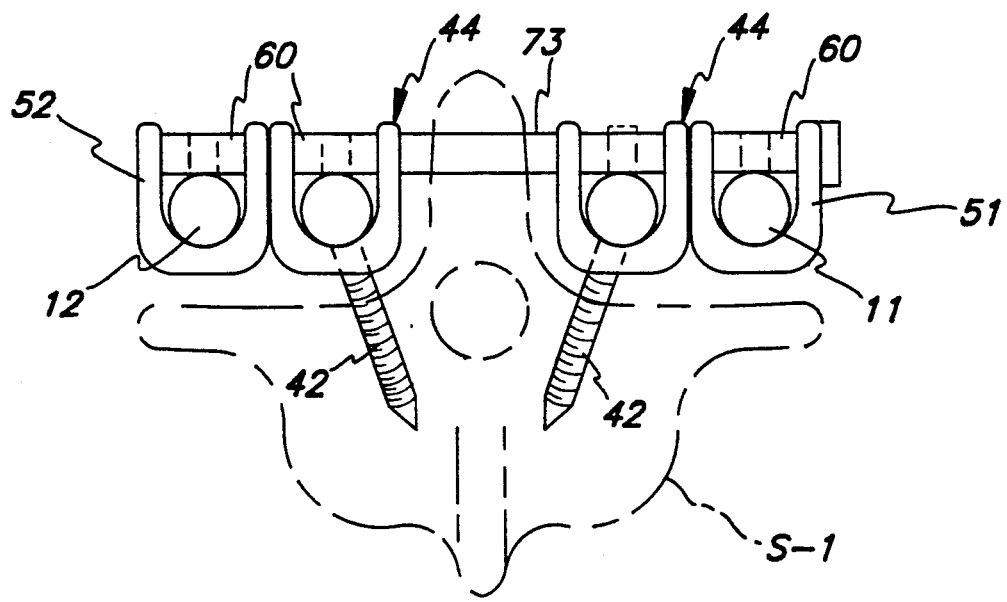
FIG. 10 is a somewhat schematic view, in transverse cross section, of a vertebra having a pair of convergent bone screws and a cross bar attached thereto, producing a delta configuration and achieving a mechanical lock in accordance with one aspect of the invention.

As indicated in FIG. 9, the screw can pivot or tilt about the longitudinal axis or the T-shaped head 43 in the screw coupler, which axis, as seen in FIG. 1, is generally parallel to the axis of the rod 11 or 12 to which the screw is attached. This enables the bone screws 40 and 41 to be screwed into the pedicle of the vertebra or body of the sacrum such that the screws converge toward one another, and in conjunction with the cross bar form a delta configuration. Thus, the screws grip a wedge-shaped section of bone between them, defining a mechanical lock and affording a much stronger purchase on the bone than could be obtained by the screw threads alone.

A first rod coupler 70 extends between the rods 11 and 12 just above the level of attachment of the bone screws, and is secured to the respective rods at its opposite ends by use of couplers 71 and 72, constructed identically to the couplers 5 and 52 used in association with the bone screw couplers. A cross bar 73 of appropriate length for the anatomy of the patient being instrumented extends between the couplers 71 and 72 and is secured in position on the rods 11 and 12 by set screws 74 and 75, respectively.

A second rod coupler 80 extends between the rods 11 and 12 in spaced relationship above the first rod coupler, and is constructed identically to the first rod coupler. Accordingly, further description of this rod coupler will not be given. It is sufficient to note that the two rod couplers form a quadrilateral construct with the rods 11 and 12, maintaining the rods in appropriately spaced relationship on laterally opposite sides of the spine. This quadrilateral construct defines a "ladder" configuration, stabilizing the rods 11 and 12 both torsionally and in the frontal plane. Moreover, the cross bars function conjointly with the convergent bone screws to form the mechanically locked delta configuration described previously, and eliminates the need for distraction to achieve fixation.

A third neutral hook 90, identical in construction to the hooks 20 and 21 previously described, is secured on the rod 11 immediately above the second rod coupler 80. This third neutral hook is oriented with its hook opening upwardly or toward the head of the patient, and in the construct shown is intended to engage on the caudal side of the right lamina of the L-4 lumbar vertebra, as viewed from the dorsal side of the spine. As in the previous examples, this hook is secured to the rod by use of the hook bar 27 and set screw 30.

Second and third hook configurations 100 and 110, respectively, are secured on the cephalad end of the rod 12 immediately above the second rod coupler 80, for gripping engagement on both the cephalad and caudal surfaces of the left lamina of the L-4 lumbar vertebra. This engagement both above and below the lamina of this vertebra maintains the instrumentation in proper engagement with the spine during bending movements of the patient.

The second hook configuration 100 is a down-angle or downwardly opening hook and has a curved anterior wall 101 (see, FIG. 11) and a pair of spaced a part, parallel side walls 102 and 103, (see, FIG. 2) with aligned openings therethrough just as in the previously described hooks 20, 21 and 90. However, in this configuration the hook opening is defined by a hook or lip 106 that is inclined in an anterior direction at about a 45° angle, and a complementally shaped posterior wall 107 that extends parallel to the lip 106 in spaced relationship thereto.

Figure 11:
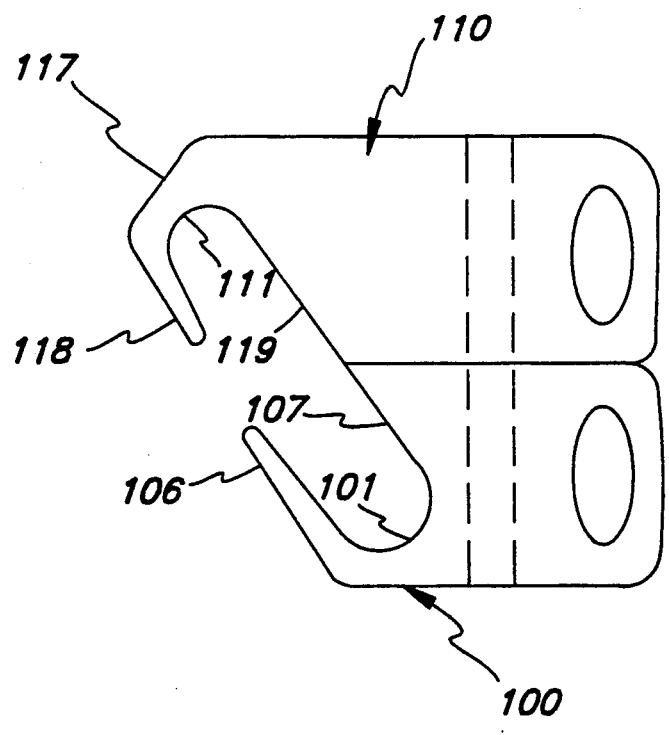
FIG. 11 is a view in side elevation of a pair of mated hooks, wherein each hook has a different configuration to enable customization or optimizing of the purchase of the hooks on differently shaped lamina.

Third hook configuration 110 is an up-angle or upwardly opening hook that also has a curved anterior wall 111 (see, FIG. 11) and a pair of spaced apart, parallel side walls 112 and 113 (see, FIG. 2), with aligned openings therethrough just as in the previously described hooks. However, in this configuration the hook opening is defined by a hook or lip 116 that includes a first section 117 extending downwardly in an anterior direction at about a 45° angle, and terminating in a second section or tip 118 that extends downwardly in a posterior direction perpendicular to the first section. A complementally shaped posterior wall 119 extends parallel to the tip 118 in spaced relationship thereto, and as seen in FIG. 11 has a considerable length.

All of the hooks and couplers have essentially U-shaped bodies open toward the posterior side, whereby when the hook bars and/or cross bars are removed, the rods can simply be laid into the hooks and couplers from the posterior side thereof. Moreover, the hook and coupler bodies, particularly the curved anterior wall, spaced side walls and oval shaped openings, are all virtually identical. This enables the hooks and couplers to be mated and organized on the rods in any order, right-side-up or inverted, and in any combination.

Further, the various couplers and hooks are able to rotate on the rods 11 and 12, even when the set screw is partially tightened to prevent axial translation of the hooks and/or couplers along the rod. By loosening the set screws, the hooks and/or couplers may be easily moved axially along the rods. This enables the surgeon to quickly and easily adapt the instrumentation to the different anatomies of different patients. This ability of the rods to rotate in the hooks and/or couplers has the additional advantage of enabling the instrumentation to be used to derotate a scoliotic curve.

Additionally, and as noted earlier herein, the cross bars are provided in a multiplicity of lengths, varying by one-half diameter of the set screw from one size to the next. This enables the surgeon to very closely match the width of the finished construct to the anatomy of a particular patient, and eliminates the stress which would otherwise be imposed on the components by a too-wide or too-narrow construct for the anatomy of the particular patient.

Figure 12:
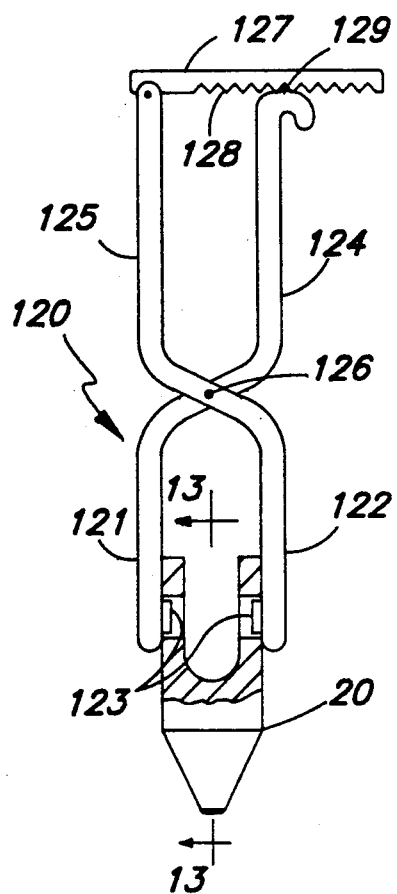
FIG. 12 is a side view, with portions in section, of a hook and associated hook holder for use in placing the hooks used in the invention.
Figure 13:
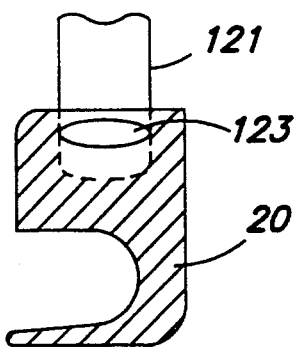
FIG. 13 is an enlarged, fragmentary view, with portions broken away, taken along line 13—13 in FIG. 12.

In order to facilitate handling and placement of the hooks, a unique hook holder 120 is provided (FIGS. 12 and 13). This tool is a scissor- or forceps-like device, and comprises a pair of opposed jaws 121 and 122 having a shaped projection 123 on the confronting faces for mating engagement in the aligned openings in the various hooks shown here as a neutral hook 20. The jaws are manipulated toward and away from one another by elongate handles 124 and 125, operating through a pivot 126. A pivoted latching bar 127 is carried on the distal end of one of the handles 125, and has a serrated undersurface 128 which cooperates with a tooth 129 on the distal end of the other handle 124 to latch the handles and thus the jaws in any of a plurality of positions, and securing the grip of the tool on the hook until released by the surgeon or an assistant.

Insertion of the bone screws 40, 41, etc., is accomplished by use of a special threaded driver 140. This tool resembles a screwdriver, with a handle 141 and elongate shank 142 extending axially therefrom. However, rather than a screwdriver blade on the end of the shank, the distal end of the shank is externally threaded at 143. This threaded end is mated with the threaded opening 31 in the hook bar 27, whereby the threaded end of the driver may be engaged in the threaded opening of the hook bar to securely engage the driver with the bone screw/coupler/hook bar construct. The tool may then be manipulated similarly to a screwdriver to rotate the screw and its coupler until the screw is inserted into the pedicle of the vertebra. The driver is then disengaged from the opening 31 to enable the bone screw and its coupler to be attached to the rest of the instrumentation.

Figure 15:
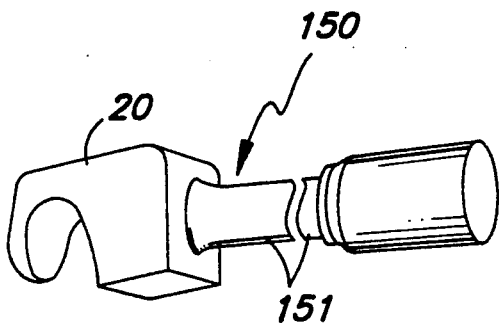
FIG. 15 is a perspective view of a trial hook tool for templating the lamina of the vertebra prior to application of an appropriate hook.
Figure 14:
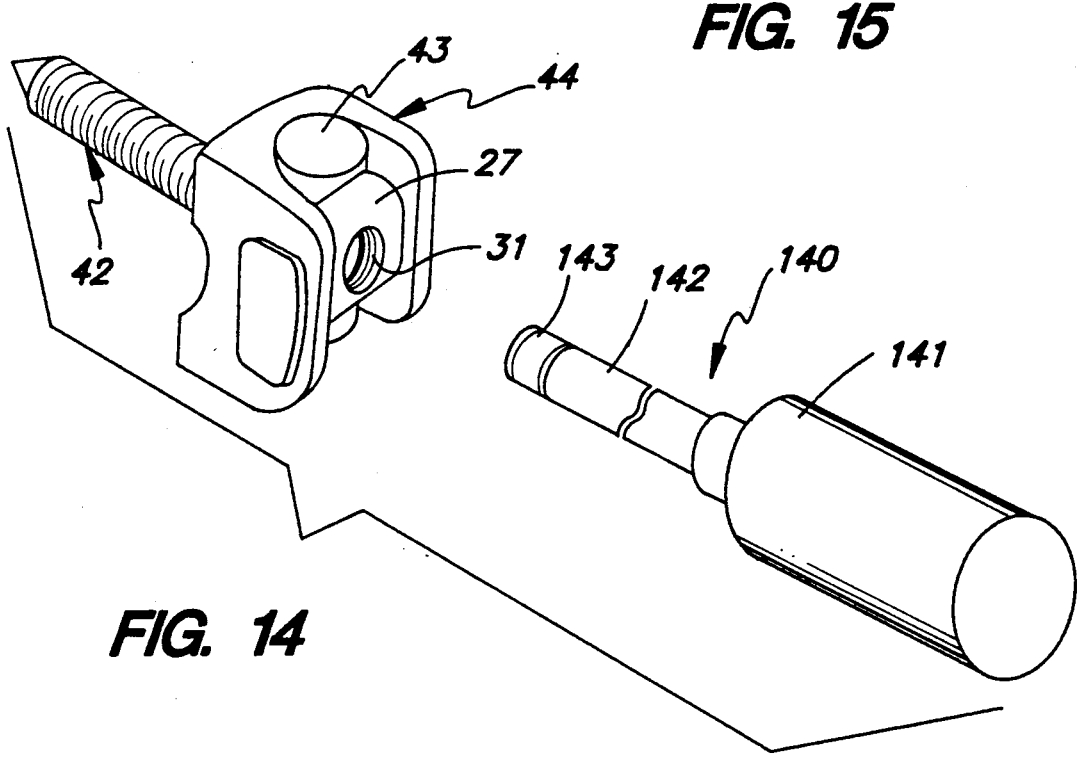
FIG. 14 is an exploded perspective view, with portions broken away, of a bone screw coupler, bone screw and threaded driver for inserting the bone screw in accordance with the invention.
Figure 16:
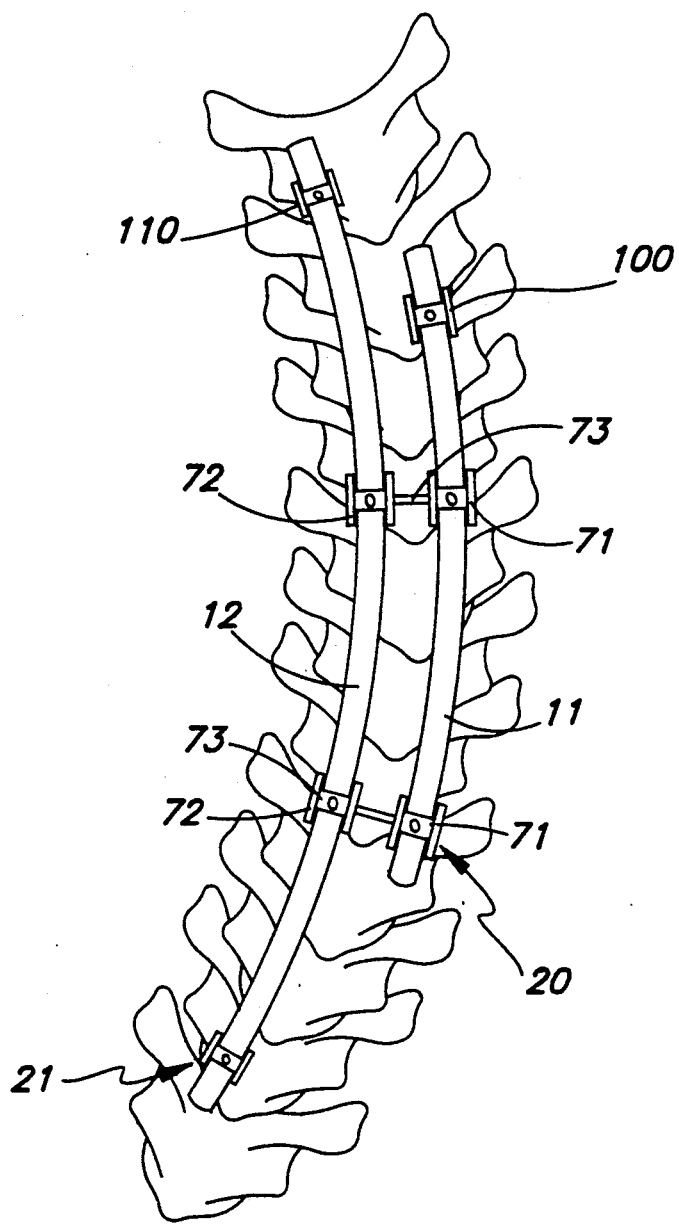
FIG. 16 is a somewhat schematic dorsal view of one form of the instrumentation of the invention shown attached to a spine.
Figure 17:
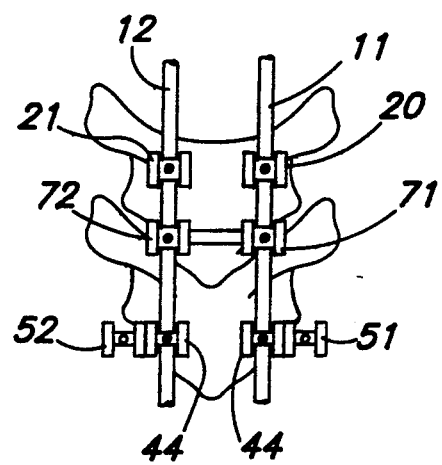
FIG. 17 is a slightly enlarged view similar to FIG. 16, showing a part of the instrumentation of the invention as it is applied to one of the vertebrae.

Trial hooks are used to template the lamina of the vertebrae prior to selection and use of an appropriate hook 20, 100 or 110. These trial hooks are in the form of a tool 150 (FIG. 15), and comprise one each of the different hook configurations, with two different sizes for each configuration. The tool 150 shown in FIG. 15 is a trial hook for the neutral hook configuration 20, and rather than the spaced, parallel side walls 25 and 26 provided on the hook used in the final construct, has a solid body with a permanently attached handle 151. In use, an approximately sized trial hook is selected by the surgeon, based on his observation of the lamina to be templated, and the trial hook is seated on the lamina using a mallet and driver (not shown). The trial hook should fit snugly on the lamina, and each of the three surfaces of the hook opening should contact a corresponding surface of the lamina. When an appropriately sized and configured trial hook has been found, a correspondingly sized and configured hook for us in the final construct is selected by matching it to the trial hook.

Instrumentation of the Spine Using the System of the Invention

The surgeon should approach the spine in his usual and customary method, exposing the spinous processus, lamina, facets and transverse processus of the involved spinal segments, after which the spine may be instrumented with the system of the invention.

The system of the invention offers screws that ar cannulated, and at the surgeon's preference, can be inserted with the aid of fluoroscopy or by exposure of the pedicle. The following description will be for the pedicle exposure method.

After exposing the pedicle and choosing the appropriate point of entry into the pedicle, the cortex is broached with a pedicle probe (not shown). The first five millimeters of the pedicle are entered with this probe, followed by hand drilling of the pedicle in a slow, circular motion to an appropriate depth, and then driven into the body of the vertebra to an appropriate depth. The position and depth should be confirmed radiologically and once the appropriate depth has been obtained, a depth gauge (not shown) is used to determine the screw length. The appropriate length screw is then chosen in preparation for insertion.

The appropriate length screw is placed in the screw coupler 44, a hook bar 27 is inserted through the aligned openings in the coupler, and the threaded driver is engaged with the threaded opening 31 in the hook bar. An open end wrench (not shown) is used to hold the screw/coupler construct while the driver is being tightened in the opening 31 in the cross bar.

The screws 42 are self tapping. However, a pilot hole may be pre-tapped in the pedicle with an appropriate mated tap (not shown), if desired. The pedicle tap depth may be measured with a suitable guide (not shown) such as used for guiding the depth of insertion of the drill bit during the drilling procedure.

The construct formed by the driver 140, screw 40, screw coupler 44 and hook bar 27 is manipulated with the driver to screw the construct into the pedicle to fully engage all of the threads on the shank 42 of the bone screw. The driver is then removed from the threaded opening 31 in the hook bar, while the construct is stabilized with a wrench. The hook bar 27 is also then removed from the coupler 44. This procedure is repeated on the contralateral side. The surgeon then repeats these steps for the number of levels to be instrumented with screws.

Prior to templating the lamina with the trial hooks 150, each lamina should be made square with a small laminotomy at its inferior lateral corners. The ligamentum flavum should be elevated off the lamina in a subperiosteal manner to allow proper seating of the hook.

When instrumenting the spine from the thoracic to L-5 lumbar lamina, the most cephalad and caudal lamina must be captured unilaterally with appropriately mated hooks. When the spine is instrumented with the inclusion of the sacrum, the sacral segment is instrumented with bilateral laminar hooks and bilateral bone screws inserted into the S-1 pedicle.

The instrumentation shown in the present instance is from the sacrum to the L-4 lumbar vertebra. The instrumentation is most easily started at the sacrum by templating the S-1 lamina with an appropriate trial hook. Next, the most proximally instrumented lamina is templated, in this case the L-4 lamina.

The lamina of L-4 is exposed unilaterally at its most cephalad edge and a small laminotomy is used to square off the lateral-most border of the lamina. After the ligamentum flavum has been freed, the appropriate trial hook is selected. This is usually the up-angled hook configuration 110. Once the laminar hook is found to be well seated, the caudal edge of the L-4 lamina is exposed in a similar manner, this being done bilaterally. Appropriate hooks are applied to either side of the midline. In this construct, the down-angled hook configuration 100 is chosen.

At this point the surgeon has determined the proper hook size and configuration for use in the construct.

The length of the rods 11 and 12 to be used is determined by utilization of a flexible rod template (not shown). Rods of appropriate length are selected from pre-cut rods or they are cut to size. After an appropriate length rod is selected, a lordotic curve may be applied in a conventional manner, if needed.

The previously chosen sacral hook 21, hook bar 27 and set screw 30 are assembled on a rod 12, with the hook engaged against the caudal end 14 of the rod. The set screw is partially tightened so that the sacral hook 21 can be rotated on the rod but not moved axially on the rod. Next, a coupler 72 and an appropriate length cross bar 73 are mounted on the rod and allowed to abut the previously mounted sacral hook 20. The set screw of the coupler is then tightened sufficiently to prevent axial movement of the coupler on the rod but yet enabling the sacral to be rotated about the axis of the rod.

The lamina of L-4 is approached and tricortical capturing of the lamina is performed unilaterally with the previously chosen hooks 100 and 110. These are seated onto the lamina and held in position by use of the hook holders 120. The inferior and superior hooks of the same lamina are held simultaneously, while the rod, coupler and sacral hook construct is mounted onto the lamina of S-1. The rods of this construct are then laid into the open slots of the hooks 100 and 110, which have been previously seated on the L-4 lamina.

Each hook holder is sequentially removed after a hook bar and set screw have been applied to the hooks 100 and 110 to maintain them in position. This step is repeated for each laminar hook.

Once the construct is formed, the lordotic curve of the rod is rotated appropriately in the sagittal plane and all set screws are tightened but not torqued.

The process is repeated for the contralateral side, keeping in mind that the L-4 lamina is captured unilaterally. In this case an up-angled hook 110 has previously been applied to the opposite side.

Distractors, not shown, can be used at this point to maintain appropriate tension between the inferiorly down-angled hook 100 of L-4, and the neutral hook 21 of the sacrum. It must be remembered that the system does not rely on distraction for its stability, and that only enough distraction should be applied to hold the construct in position.

The set screw is removed from the cross bar 73 of the previously mounted coupler 72, and an appropriate length cross bar 73 is used to connect the mated couplers 71 and 72 on the rods 11 and 12. If the previously mounted cross bar 73 is of inappropriate length, it may be replaced at this time. This maneuver is performed to include as many transverse cross bars as needed. In the present construct, only two are needed to complete the quadrilateral frame.

The sacral hooks 20 and 21 will now have oriented themselves to the slope of the sacral lamina in the transverse plane, and their set screws may be tightened, but not torqued.

The most proximal coupler 71, 72 and transverse cross bar 73 construct is slid proximally on the rods to allow the application of couplers 51, 52 that will be mated to the previously installed bone screw couplers 44, and secured by cross bars 60 and set screws.

The construct is now complete and if no changes are necessary, each set screw is torqued with a torque wrench while an assistant stabilizes the construct with a rod holder (not shown). The torque wrench ensures that an appropriate amount of torque is applied without over-torquing the system or stripping the set screws. Use of the torque wrench to torque the set screws at each of the attachments produces a constant holding force throughout the construct.

The modularity of the system affords the surgeon great flexibility in configuring the internal fixation to the anatomic constraints without compromising fixation capabilities. It also allows customization of the hook and screw fixation and does not limit or commit the surgeon to either fixation mode. Further, components can be added after a construct has been completed. This gives the surgeon the ability to instrument any additional segments at a later setting without having to dismantle the existing construct.

The ability of the couplers and hooks to pivot on the rods makes it possible to use the construct to derotate a scoliotic curve, thus providing additional correction capabilities. This derotation can be performed with a hook construct, a bone screw construct, or a hybrid construct including a combination of hooks and bone screws.

The slotted or open back hook and coupler design facilitates instrumentation by allowing the hooks to be preseated onto the lamina, followed by application of the rods into the slots of the hooks and couplers, rather than having to pre-mount the hooks onto the rods. The same ease of instrumentation is also provided by the screws, which are affixed to the bone prior to the application of the rod(s). The locking mechanism, i.e., the set screws and bars, are easily accessible from a dorsal approach, adding further to the ease of use of the system.

The unique, multiple hook configurations permit tricortical capturing of the lamina and avoids the single point laminar contact that is sometimes obtained with prior art systems. The superior fit of the hooks onto the lamina also minimizes intrusion into the spinal canal, and the angled hook configurations of hooks 100 and 110 compensates for the "shingling" of the vertebrae in the spine. This also makes it possible for the surgeon to instrument the system without having to contour a lordotic curve into the rod.

The use of screws in the sacral pedicle permits fixation of the system to include the sacrum, and the use of the transverse cross bars not only forms a quadrilateral construct but also cooperates with the convergent bone screws to form a delta configuration, obtaining purchase on the bone by gripping a wedge shaped section of bone and forming a mechanical lock. This provides a much more secure purchase than relying solely upon engagement of the threads of the screws in the bone.

Further, the ability of the heads of the screws to pivot in the screw couplers permits the surgeon to place the screws in such a manner that they need not be at the same level from the laminar margin, and at the same time allows coupling of the screw to the coupler via the transverse cross bars. The ability of the screw coupler, screws, and couplers to rotate further enables the screws to be inserted in optimal position relative to the pedicle for maximum purchase, and minimizes pedicle cut-out. This same flexibility also permits the bone screws to be coupled to the rod with the use of various length transverse cross bars, thereby avoiding preloading of the bone screws.

The system of the invention remains medialized and is of low profile, allowing the spinal surgeon to perform his decortication and application of the bone graft as a last step in the fusion. This reduces intraoperative bleeding and morbidity associated with the surgery by not having to work in a bloody field.

Although the invention has been described with reference to a particular embodiment, it is to be understood that this embodiment is merely illustrative of the application of the principles of the invention. Numerous construct configurations may be made therein and other arrangements may be devised without departing from the spirit and scope of the invention.

I claim:

1. A surgically implantable system for correction of a spinal abnormality which comprises two rods adapted to extend alongside vertebrae of a spinal section in need of correction first means for engagement in a preselected first position on a first side of a spine to at least one vertebra of said spinal section said first position being preselected to provide a force in a first axial direction relative to said spine when said system is implanted and assembled second means for engagement in a preselected second position on said first side of said spine to at least one vertebra of said spinal section said second position being preselected to provide a force in a second axial direction relative to said spine when said system is implanted and assembled said first engagement means having first fastening means and said second engagement means having second fastening means, said first and second fastening means being operable when said system is surgically implanted and assembled to provide attachment of said first rod to said first and second engagement means at axially adjustable locations and to enable or to preclude relative movement between said first rod and either of said first and second fastening means;

third means for engagement in a preselected third position to at least one vertebra of said spinal section said third position being preselected to provide a force in a third axial direction relative to said spine when said system is implanted and assembled fourth means for engagement in a preselected fourth position to at least one vertebra of said spinal section said fourth position being preselected to provide a force in a fourth axial direction relative to said spine when said system is implanted and assembled said third engagement means having third fastening means and said fourth engagement means having fourth fastening means said third and fourth fastening means being operable when said system is surgically implanted and assembled to provide attachment of said second rod to said third and fourth engagement means at axially adjustable locations and to enable or to preclude relative movement between said second rod and either of said third and fourth fastening means at least one coupler rod extending between said first and said second rod, said coupler rod adjustably secured along the length of said first rod and also adjustably secured along the length of said second rod to maintain said first rod and said second rod in adjustably fixed spaced relationship from each other with respect to said spine by set screws.

2. A system, as claimed in claim 1, wherein:

at least one of said first means, second means, third means or said fourth means comprises a hook having a projection on an anterior side thereof for engagement over a lamina of a vertebra.

3. A system, as claimed in claim 2, further comprising a plurality of hooks of different configuration for complemental hooking engagement over differently configured lamina.

4. A system, as claimed in claim 3, comprising at least six differently shaped and sized hooks for complemental hooking engagement on differently shaped and sized lamina.

5. A system, as claimed in claim 3, comprising at least three differently shaped hooks for complemental hooking engagement on differently shaped lamina.

6. A system, as claimed in claim 5, wherein said differently shaped hooks are of different sizes for complemental hooking engagement on differently sized lamina.

7. A system, as claimed in claim 1, wherein:

at least one of said first, second, third or fourth engagement means includes a screw adapted for insertion into the pedical of a vertebra said screw being carried by a screw coupler.

8. A system, as claimed, in claim 7, wherein:

the screw is carried by a screw coupler having a U-shaped open back.

9. A system, as claimed in claim 8, wherein:

said screw has an elongate threaded shank with a T-shaped head, and said U-shaped open back of said screw coupler has an anterior wall with a pair of spaced apart side walls extending therefrom in a posterior direction, defining a receiving recess for a cross bar; and said anterior wall has an opening therethrough for receiving said threaded shank of said screw, with the head of said screw received between said side walls of said recess.

10. A system as claimed in claim 1, wherein:

each said first, second, third and fourth fastening means includes a receiving recess for said rod first and second rod, each of said receiving recesses comprises an anterior wall with a pair of spaced apart side walls extending therefrom in a posterior direction, said side walls having aligned openings therethrough; and said fastening means comprises an elongate bar extended through said aligned openings in a direction transverse to said recess, said bar being provided with a set screw for engagement with said rod.

11. A system, as claimed in claims 4 or 9, wherein:

each of said first, second, third and fourth fastening means includes a receiving recess for said first or second rod each of said receiving recesses comprises an anterior wall with a pair of spaced apart side walls extending therefrom in a posterior direction, said side walls having aligned openings therethrough; and said fastening means comprises an elongate bar extended through said aligned openings in a direction transverse to said recess, said bar being provided with a set screw for engagement with said rod.

12. A system, as claimed in claim 1, further comprising two coupler rods extending between and secured to said first and second rods toward cephalad and caudal ends, respectively, of said first and second rods, defining a quadrilateral construct for torsional stability of said first and second rods.

13. A system, as claimed in claim 12, wherein: for each coupler rod there are a pair of rod couplers each rod coupler includes a pair of U-shaped bodies having an anterior wall and a pair of spaced apart side walls extending in a posterior direction therefrom, the U-shaped bodies of each pair of rod couplers being secured in laterally opposed relationship on said first and second rods; and said coupler rod extending between and secured to the two laterally opposed U-shaped bodies of each pair of said rod couplers.

14. A system, as claimed in claim 13, further comprising coupler fastening means engaged with said rod couplers and with said first and second rods to secure said rod couplers in position on said first and second rods, said coupler fastening means comprising said coupler rods and set screws extended therethrough to secure the rod couplers to the first and second rods.

15. A system, as claimed in claim 8, wherein:

said screw has an elongate threaded shank with a T-shaped head, and said screw coupler has an anterior wall with a pair of spaced apart side walls extending therefrom in a posterior direction, defining a recess, said side walls having aligned openings therethrough;

said anterior wall has an opening therethrough for receiving said threaded shank of said screw, with the head of said bone screw received between the side walls of the U-shaped body; and a cross bar extends across said U-shaped body between said side walls and through said aligned openings for retaining said bone screw in position in said U-shaped body, said cross bar having means in a posterior surface thereof for cooperation with a tool for rotating said U-shaped body and said screw to insert said screw in a bone.

16. A system, as claimed in claim 15, wherein:

said means in said cross bar for cooperation with a tool comprises at threaded opening for engagement with a threaded driver to manipulate said screw, said threaded opening also serving as a means for receiving a set screw that extends into engagement with said T-shaped head of said screw after insertion whereby said cross bar, screw coupler and screw are mutually secured.

17. A system, as claimed in claim 9, wherein said T-shaped head of said screw is pivotable in said screw coupler, about an axis parallel to the axes of said first and second rod, with a screw and associated screw coupler secured on each of said first and second rods in opposed relationship, whereby said screws may be inserted into the pedicle of a vertebra in converging relationship to one another, defining a delta configuration with a coupler rod and thereby obtaining a mechanical, wedge shaped lock on the bone of the vertebra.

18. A system, as claimed in claim 11, wherein: said aligned openings have noncircular shape, and said elongate bar received in the openings has a corresponding noncircular cross-sectional shape whereby said elongate bar may be received in said openings in only a predetermined orientation.

19. A system, as claimed in claim 18, wherein: said elongate bar has visually and tactually discernible indicia thereon to indicate orientation.

20. A system including a plurality of vertebrae engaging means for attachment to the spine to correct and support the spine in the treatment of spinal abnormalities, comprising:
along laterally opposite sides of said spine in longitudinally spanning relationship to the section of the spine to be treated;
said vertebrae engaging means comprising a plurality of hooks adapted to be engaged with lamina of spaced vertebrae to exert force in opposed axial directions relative to the longitudinal axis of said spine to correct the abnormality, said hooks including hooks of different configuration for complemental engagement with differently configured lamina of vertebrae; and
said hooks each having a body shaped for attachment to said first rod or said second rod, and said bodies being configured so said hooks may be interchanged with one another, or inverted relative to one another, and mated in stacked relationship to one another on said first rod and said second rod, whereby different hooks may be placed differently on said first rod and said second rod for optimum purchase with lamina of different vertebrae, at least one coupler rod extending between said first rod and said second rod, said coupler rod adjustably secured along the length of said first rod and also adjustably secured along the length of said second rod to maintain said first rod and said second rod in adjustably fixed spaced relationship from each other with respect to said spine by set screws.

21. A system, as claimed in claim 20, wherein: there is at least one screw for insertion with the pedicle of the vertebrae, said screw being carried by a screw coupler, and said screw coupler being secured to said first rod or said second rod, wherein said system has the versatility of being able to use any one of several differently configured hooks and bone screws in any position in mating engagement with one another on said first rod and said second rod.

22. A surgically implantable system for correction of a spinal abnormality which comprises at least one rod adapted to extend alongside the vertebrae of a spinal section in need of correction
first means for engagement in a preselected position with a lamina of at least one vertebrae in a first portion of said spinal section
said position being preselected to provide a force in a first axial direction relative to a spine when said system is implanted and assembled
second means for engagement in a preselected position with a lamina of at least one vertebra in a second portion of said spinal section
said position being preselected to provide a force in a second axial direction relative to said spine when said system is implanted and assembled
each of said first means and said second means being provided with a receiving recess for said rod, said recess facing posteriorly when said first and second means are engaged with said laminae, and
fastening means attached to said first and second means said fastening means being operable when said system is surgically implanted and assembled to provide attachment of said rod to said first and second means at axially fixed locations and to enable or to preclude relative movement between said rod and either of said first and second means,
said receiving recess for said rod comprises an anterior wall with a pair of spaced apart side walls extending therefrom in a posterior direction, said side walls having aligned openings therethrough; and
said fastening means comprises an elongate bar extended through said aligned openings in a direction transverse to said recess, said bar being provided with a set screw for engagement with the rod.

23. A surgically implantable system for correction of a spinal abnormality which comprises
at least one rod adapted to extend alongside the vertebrae of a spinal section in need of correction
first means for engagement in a preselected position with a lamina of at least one vertebra in a first portion of said spinal section
said position being preselected to provide a force in a first axial direction relative to a spine when said system is implanted and assembled
second means for engagement in a preselected position with a lamina of at least one vertebra in a second portion of said spinal section
said position being preselected to provide a force in a second axial direction relative to said spine when said system is implanted and assembled
each of said first means and said second means being provided with a receiving recess for said rod, said recess facing posteriorly when said first and second means are engaged with said laminae, and
fastening means attached to said first and second means said fastening means being operable when said system is surgically implanted and assembled to provide attachment of said rod to said first and second means at axially fixed locations and to enable or to preclude relative movement between said rod and either of said first and second means,
at least one of said first means or said second means comprises a hook having a projection on an anterior side thereof for engagement over a lamina of the vertebra, and there are a plurality of hooks of different configuration for complemental hooking engagement over differently configured lamina, said plurality of hooks comprising at least six differently shaped and sized hooks for complemental engagement one differently shaped and sized lamina, wherein, said recess for said rod comprises an anterior wall with a pair of spaced apart side walls extending therefrom in a posterior direction, said side walls having aligned openings therethrough; and said fastening means comprises an elongate bar extended through said aligned openings in a direction transverse to said recess, said bar being provided with a set screw for engagement with a rod.

24. A surgically implantable system for correction of a spinal abnormality which comprises at least one rod adapted to extend alongside the vertebrae of a spinal section in need of correction first means for engagement in a preselected position with a lamina of at least one vertebra in a first portion of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, at least one of said first means or said second means comprises a hook having a projection on an anterior side thereof for engagement over a lamina of the vertebra, and there are a plurality of hooks of different configuration for complemental hooking engagement over differently configured lamina, said plurality of hooks comprising at least six differently shaped and sized hooks for complemental engagement on differently shaped and sized lamina, wherein said aligned openings have a noncircular shape, and the elongate bar received in the openings has a corresponding noncircular cross-sectional shape whereby the bar may be received in the openings in only a predetermined orientation.

25. A surgically implantable system for correction of a spinal abnormality which comprises at least one rod adapted to extend alongside the vertebrae of a spinal section in need of correction first means for engagement in a preselected position with a lamina of at least one vertebra in a first portion of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, at least one of said first means or said second means comprises a hook having a projection on an anterior side thereof for engagement over a lamina of the vertebra, and there are a plurality off hooks of different configuration for complemental hooking engagement over differently configured lamina, said plurality of hooks comprising at least six differently shaped and sized hooks for complemental engagement on differently shaped and sized lamina, wherein said bar has visually and tactually discernible indicia thereon to indicate orientation.

26. A surgically implantable system for correction of a spinal abnormality which comprises at least one rod adapted to extend alongside the vertebrae of a spinal section in need of correction first means for engagement in a preselected position with a lamina of at least one vertebra in a first portion of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, at least one of said first or second means includes a screw adapted for insertion into the pedicle of the vertebra, said screw is carried by a screw coupler having a U-shaped open back and said screw has an elongate threaded shank with a T-shaped head, and said screw coupler has an anterior wall with a pair of spaced apart side walls extending therefrom in a posterior direction, defining receiving recess therefrom in a posterior direction, defining receiving recess for said rod; and said anterior wall has an opening therethrough for receiving said threaded shank of said screw, with the head of said screw received between the side walls of said recess, wherein, said recess for said rod comprises an anterior wall with a pair of spaced apart side walls extending therefrom in a posterior direction, said side walls having aligned openings therethrough; and said fastening means comprises an elongate bar extended through said aligned openings in a direction transverse to said recess, said bar being provided with a set screw for engagement with the rod.

27. A surgically implantable system for correction of a spinal abnormality which comprises at least one rod adapted to extend alongside the vertebrae of a spinal section in need of correction first means for engagement in a preselected position with a lamina of at least one vertebra in a first portion of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, and at least one of said first or second means includes a screw adapted for insertion into the pedicle of the vertebra, said screw is carried by a screw coupler having a U-shaped open back and said screw has an elongate threaded shank with a T-shaped head, and said screw coupler has an anterior wall with a pair of spaced apart side walls extending therefrom in a posterior direction, defining receiving recess for said rod; and said anterior wall has an opening therethrough for receiving said threaded shank of said screw, with the head of said screw received between the side walls of said recess, said recess for said rod comprises an anterior wall with a pair of spaced apart side walls extending therefrom in a posterior direction, said side walls having aligned openings therethrough; and said fastening means comprises an elongate bar extended through said aligned openings in a direction transverse to said recess, said bar being provided with a set screw for engagement with the rod, wherein, said aligned openings have a noncircular shape, and the elongate bar received in the openings has a corresponding noncircular cross-sectional shape whereby the bar may be received in the openings in only a predetermined orientation.

28. A surgically implantable system for correction of a spinal abnormality which comprises at least one rod adapted to extend alongside the vertebrae of a spinal section in need of correction first means for engagement in a preselected position with a lamina of at least one vertebra in a first position of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, and at least one of said first or second means includes a screw adapted for insertion into the pedicle of the vertebra, said screw is carried by a screw coupler having a U-shaped open back and said screw has an elongate threaded shank with a T-shaped head, and said screw coupler has an anterior wall with a pair of spaced apart side walls extending therefrom in a posterior direction, defining receiving recess for said rod; and said anterior wall has an opening therethrough for receiving said threaded shank of said screw, with the head of said screw received between the side walls of said recess, said recess for said rod comprises an anterior wall with a pair of spaced apart side walls extending therefrom in a posterior direction, said side walls having aligned openings therethrough; and said fastening means comprises an elongate bar extended through said aligned openings in a direction transverse to said recess, said bar being provided with a set screw for engagement with the rod, said aligned openings have a noncircular shape, and the elongate bar received in the openings has a corresponding noncircular cross-sectional shape whereby the bar may be received in the openings in only a predetermined orientation, wherein, said bar has visually and tactually discernible indicia thereon to indicate orientation.

29. A surgically implantable system for correction of a spinal abnormality which comprises at least one rod adapted to extend alongside the vertebrae of a spinal section in need of correction first means for engagement in a preselected position with a lamina of at least one vertebra in a first portion of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, and at least one of said first or second means includes a screw adapted for insertion into the pedicle of the vertebra, said screw is carried by a screw coupler having a U-shaped open back, wherein, said screw has an elongate threaded shank with a T-shaped head, and said screw coupler has an anterior wall with a pair of spaced apart side walls extending therefrom in a posterior direction, defining a recess, said side walls having aligned openings therethrough;

said anterior wall has an opening therethrough for receiving said threaded shank of said screw, with the head of said bone screw received between the side walls of the U-shaped body; and an elongate bar extends across said U-shaped body between said side walls and through said aligned openings for retaining said bone screw in position in said body, said bar having means in a posterior surface thereof for cooperation with a tool for rotating said screw to insert it into a bone.

30. A surgically implantable system for correction or a spinal abnormality which comprises at least one rod adapted to extend alongside the vertebrae of a spinal section in need of correction first means for engagement in a preselected position with a lamina of at least one vertebra in a first portion of said spinal section said position being preselected to provide a force in a first axial direction relative to a spine when said system is implanted and assembled second means for engagement in a preselected position with a lamina of at least one vertebra in a second portion of said spinal section said position being preselected to provide a force in a second axial direction relative to said spine when said system is implanted and assembled each of said first means and said second means being provided with a receiving recess for said rod, said recess facing posteriorly when said first and second means are engaged with said laminae, and fastening means attached to said first and second means said fastening means being operable when said system is surgically implanted and assembled to provide attachment of said rod to said first and second means at axially fixed locations and to enable or to preclude relative movement between said rod and either of said first and second means, and at least one of said first or second means includes a screw adapted for insertion into the pedicle of the vertebra, said screw is carried by a screw coupler having a U-shaped open back, said screw has an elongate threaded shank with a T-shaped head, and said screw coupler has an anterior wall with a pair of spaced apart side walls extending therefrom in a posterior direction, defining a recess, said side walls having aligned openings therethrough;

said anterior wall has an opening therethrough for receiving said threaded shank of said screw, with the head of said bone screw received between the side walls of the U-shaped body; and an elongate bar extends across said U-shaped body between said side walls and through said aligned openings for retaining said bone screw in position in said body, said bar having means in a posterior surface thereof for cooperation with a tool for rotating said screw to insert it into a bone wherein, said mean sin said bar for cooperation with a tool comprises a threaded opening for engagement with a threaded driver to manipulate said bone screw, said threaded opening also serving as a means for receiving a set screw that extends into engagement with the T-shaped head of the screw after the insertion whereby the bar, screw coupler and screw are mutually secured.

* * * * *